United States Patent
Fontenot et al.

[11] Patent Number: 5,863,202
[45] Date of Patent: Jan. 26, 1999

[54] DEVICE AND METHOD FOR TREATMENT OF DENTITION

[76] Inventors: Mark G. Fontenot, 229 Marilyn Dr., Lafayette, La. 70503-3968; Wendt L. Withers, 303 Champ Elysee, Maurice, La. 70555

[21] Appl. No.: 694,445

[22] Filed: Aug. 12, 1996

Related U.S. Application Data

[63] Continuation-in-part of Ser. No. 980,635, Nov. 24, 1992, abandoned, and a continuation-in-part of Ser. No. 213,039, Mar. 15, 1994, Pat. No. 5,575,654.

[51] Int. Cl.$^6$ .................................................. A61C 5/00
[52] U.S. Cl. .................................................. 433/215; 433/80
[58] Field of Search ................................ 433/215, 80, 77, 433/37, 38, 41; 206/570, 368, 369, 63.5, 564, 83; 128/859, 861

[56] References Cited

U.S. PATENT DOCUMENTS

| | | | |
|---|---|---|---|
| 3,339,547 | 9/1967 | Drabkowski | 128/260 |
| 3,527,219 | 9/1970 | Greenberg | 433/215 |
| 3,624,909 | 12/1971 | Greenberg . | |
| 4,138,814 | 2/1979 | Weitzman | 433/215 |
| 4,180,159 | 12/1979 | Tanaka | 206/63.5 |
| 4,226,851 | 10/1980 | Sompayrac | 424/53 |
| 4,661,070 | 4/1987 | Friedman | 433/203.1 |
| 4,687,663 | 8/1987 | Schaeffer | 424/52 |
| 4,763,791 | 8/1988 | Halverson et al. | 206/570 |
| 4,788,052 | 11/1988 | Ng et al. | 424/53 |
| 4,950,163 | 8/1990 | Zimble | 433/215 |
| 4,952,143 | 8/1990 | Becker | 433/32 |
| 4,968,251 | 11/1990 | Darnell | 433/216 |
| 4,983,380 | 1/1991 | Yarborough | 424/52 |
| 4,983,381 | 1/1991 | Zaragoza | 424/53 |
| 4,990,089 | 2/1991 | Munro | 433/215 |
| 5,009,885 | 4/1991 | Yarborough | 433/215 |
| 5,032,178 | 7/1991 | Cornell | 106/35 |
| 5,063,940 | 11/1991 | Adell et al. | 206/63.5 |
| 5,098,303 | 3/1992 | Fisher | 433/215 |

(List continued on next page.)

OTHER PUBLICATIONS

Goldstein, Ronald E., Haywood, Van B., Heymann, Harald O. Steiner, David R., West, John D., "Bleaching of Vital and Pulpless Teeth" *Pathways of the Pulp*, 6th ed., Mosby Press.
Vari–Shade Custom Thermo–Forming Trays, Commercially available from Vari–Shade Dental Products, San Diego, California.
Pro–Brite Tooth Whitening, commercially available from eop, Inc., Minneapolis, Minnesota.
FluEze and Vital White, commercially available from CADCO, Oxnard, California.
Gerber, David A., Goldstein, Cary E., Goldstein, Ronald E., Schwartz, Kathy G., "Dentist Monitored Bleaching: A Combined Approach,"*Practical Periodontics and Aesthetic Dentistry*,vol. 3, No. 1 (Jan./Feb.1991).

*Primary Examiner*—Cary E. O'Connor
*Attorney, Agent, or Firm*—Lynette Wylie

[57] ABSTRACT

A dental device for the treatment of dental arches and periodontal tissue addressing the drawbacks of the prior art, comprising a prefabricated dental appliance composed of a non-porous polymeric material having a trough for immersing the teeth of the dental arch, the dental appliance being adaptable to fit a range of variously sized dental arches, and a premeasured amount of bleaching and/or other dental agent, which may be predispensed within the trough of the disposable dental appliance. The dental appliance of the present invention may be packaged to enclose individual or multiple units. The predispensed dental agent may be predispensed within the packaged appliances, or be sealed in the trough of the dental appliance. Alternatively, the predetermined amount of dental agent may be packaged in a separate container located adjacent to the trough orifice so that the dental agent is capable of being directly expelled into the trough of dental appliance when the seal is opened. The packaging may also contain multiple dental appliances with predispensed dental agent with which a desiccant may be included. The dental agent may also be sealed in a separate dispenser, preferably a syringe.

15 Claims, 9 Drawing Sheets

U.S. PATENT DOCUMENTS

| | | | |
|---|---|---|---|
| 5,125,834 | 6/1992 | Swan | 433/80 |
| 5,165,424 | 11/1992 | Silverman | 128/861 |
| 5,184,718 | 2/1993 | Albert | 206/63.5 |
| 5,190,168 | 3/1993 | French et al. | 433/77 |
| 5,199,567 | 4/1993 | Discko, Jr. | 206/368 |
| 5,234,342 | 8/1993 | Fisher | 433/215 |
| 5,240,415 | 8/1993 | Haynie | 433/216 |
| 5,289,919 | 3/1994 | Fischer | 433/77 |
| 5,294,434 | 3/1994 | King et al. | 424/58 |
| 5,323,787 | 6/1994 | Pratt | 433/37 |
| 5,326,685 | 7/1994 | Gaglio | 433/215 |
| 5,346,061 | 9/1994 | Newman | 206/221 |
| 5,356,291 | 10/1994 | Darnell | 433/216 |
| 5,376,006 | 12/1994 | Fischer | 433/215 |
| 5,378,465 | 1/1995 | Zeines | 424/195.1 |
| 5,445,263 | 8/1995 | Mohlenkamp et al. | 206/564 |
| 5,513,750 | 5/1996 | Rychel | 206/564 |
| 5,756,654 | 11/1996 | Fontenot | 433/215 |
| 5,855,286 | 10/1974 | Cowen | 128/861 |

5,863,202

DEVICE AND METHOD FOR TREATMENT OF DENTITION

This is a continuation in part of application Ser. No. 07/980,635 for Apparatus and Method For Lightening Teeth, which was filed on Nov. 24, 1992, now abandoned, and a continuation in part of pending application Ser. No. 08/213,039, which was filed on Mar. 15, 1994, now U.S Pat. No. 5,575,654.

FEILD OF THE INVENTION

The apparatus and method of this invention relate to dental treatments.

BACKGROUND OF THE INVENTION

Recently, home bleaching has been introduced into the dental health care market for the management of stained teeth. Home bleaching is a technique utilizing weak oxidizing agents such as a 6 to 15 percent carbamide peroxide or other peroxy compound which are delivered to the dental arch by the patient using a rigid dental appliance which is custom fabricated by a dentist or dental laboratory. Protocols outlined by dental professionals for the treatment of stained teeth employing the home bleaching technique generally recommend that the patient wear a rigid custom dental appliance for periods of up to 120 minutes per day usually over the course of several weeks, totaling between 20 to 40 hours of home bleaching time.

All currently available bleaching agents are either viscous liquids or gels. Bleaching agents are commercially available and packaged in separate dispensing containers such as bottles, syringes, and tubes. The bleaching agent is self-administered by the patient, who dispenses an estimated quantity of bleaching agent to the rigid custom dental appliance.

The exact origin of the home bleaching procedure is unclear. The earliest reports of this technique occurred in the mid-1960's when two dentists in Arkansas reported Glyoxide™, which is commercially available from Marion Merrel Dow, Inc. Glyoxide™ is an agent used in a custom dental appliance, or dental splint, for soft tissue wound healing, resulted in the desirable side effect of whitening teeth. Glyoxide™ is an over-the-counter preparation containing 10% carbamide peroxide in glycerine. These dentists switched to Proxigel™, which is commercially available from Reed & Carnrick Pharmacy after its introduction into the over-the-counter market in 1972. Proxigel™ is a combination of water, glycerine, Carbopol™ (thickening agent) and 10% carbamide peroxide.

The first report of the home bleaching procedure was published in 1989, when Haywood and Heymann reported successful bleaching using Proxigel™ in a custom fabricated dental appliance to be worn at night. In the Haywood and Heymann procedure, the bleaching agent was placed in a soft plastic, vacuum formed dental appliance for an average of 7.5 hours per night for 2 to 5 weeks. Also, in 1989, White and Brite™, which is marketed by Omni International, became the first commercially available dental bleaching agent specifically for whitening teeth. White and Brite™ is a preparation containing 10% carbamide peroxide in glycerine which is sold exclusively to dentists and sold in conjunction with custom-fitted or prescription dental appliances. Since its introduction into the dental health care market, over 20 companies have marketed similar products.

The aforementioned home bleaching techniques require two dental office visits and the fabrication of a rigid custom dental appliance. During the first office visit, impressions of the dental arches are taken, from which rigid custom-fitted dental appliances are fabricated. The use of thermoplastic films are recommended for the fabrication of rigid custom dental appliances which function to carry and deliver various home bleaching agents to the dental arches. Thermoplastic films are sold as rigid or semi-rigid sheeting and are available in various sizes and thicknesses. Some manufacturers also offer laminations of porous foams or low modulus plastics to rigid thermoplastic films.

Fabrication of rigid custom dental appliances to stone models of the dental arches necessitates heating and vacuum forming a rigid thermoplastic sheet to the stone models of a patient's dental arches. The excess sheeting is subsequently removed and the resulting rigid custom dental appliance polished and provided to the dentist for fitting to the patient's dental arches.

Dentists have traditionally utilized one of three types of dental appliances for bleaching teeth. The first type is a rigid appliance which is fitted precisely to the patient's dental arches.

A second type of rigid custom dental appliance frequently practiced by dentists is the delivery of home bleaching agents in an "oversized" rigid custom dental appliance. The dental laboratory fabrication technique for the oversized rigid dental appliance involves augmenting the facial surfaces of the teeth on the stone models with materials such as die spacer or light cured acrylics. Next, thermoplastic sheeting is heated and subsequently vacuum formed around the augmented stone models of the dental arch. The net effect of this method results in an "oversized" rigid custom dental appliance.

A third type of rigid custom dental appliance, which is used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

After consultation with the dentist and fabrication of the aforementioned dental appliance, a teeth whitening procedure utilizing the dental appliance is practiced by the patient, who then typically applies the bleaching agent daily. The patient dispenses the home bleaching agent into the rigid custom dental appliance and then places the appliance over the dental arch. Generally, the recommended treatment period ranges from 30 to 120 minutes per day. At the end of the treatment period, the dental appliance is removed, cleaned with water to remove any remaining bleaching agent, and then stored until the next application.

Unfortunately, there exist many problems with obtaining rigid custom-fabricated dental appliances. Such problems include the time and expense of making dental impressions and dental laboratory work, two office visits, and possibly reshaping poorly fitted appliances.

There exist additional drawbacks with custom bilaminated dental devices. These include occlusion and retention of bleaching agent. The rigidity of such appliances cause irritation and reduce the treatment time periods that a patent will tolerate. Furthermore, cleaning and maintenance of the foam-lined dental appliance is difficult, due to its high surface area and pore volume.

Yet further problems of oversized rigid custom dental appliance, including, but not limited to, occlusion, increased fabrication time and cost, irritation and the lip of the appliance contacting the gingival region, and decreased retention to the bleaching agent within the target area.

Such problems triggered the development of a fourth and final type of treatment regimen employed to deliver home bleaching. That regimen replaces rigid custom dental appliances with individually packaged disposable U-shaped soft foam trays saturated with a premeasured quantity of bleaching agent. Such a device is commercially available from Cadco Dental Products in Oxnard, Calif. under the trade name Vital white™. Recommended treatment protocol described in the product's package insert instructs the patient to fit the device around his or her teeth and to keep the tray in position for sixty minutes after which time it is removed and discarded. Cadco suggests that fourteen sixty-minute applications be delivered in a two week period.

Unfortunately, however, foam appliances used in home bleaching systems such as that provided by Cadco have proven to be replete with their own problems. The porous foam tray of such systems is bulky, lacks adequate structural rigidity to fit securely over the dental arches, and causes excessive salivation.

Such foam appliances fail to direct and confine the application of home bleaching agents on the surfaces of a patient's teeth, which is critical to the safety and efficacy of any dental appliance, or other medical device used in or on the human body. Furthermore, the surfaces of such foam devices, which are saturated with bleaching agent, are open and exposed to the oral cavity, and allow the elution of large quantities of bleaching agent from the device, enter the oral cavity, and be ingested by the patient. In addition, because of the discomfort associated with the moisture buildup resulting from foaming of the bleaching agent and salivation, patient compliance and acceptance is low.

Appliances constructed of materials other than foam designed to address such leak-related drawbacks pose other problems. They are rigid and tend to invade sensitive gingival tissue surrounding the dental arches. This reduces patent tolerance to bleaching, and may result in reduced bleaching time and efficacy of treatment. Further drawbacks attendant to prior art teeth bleaching methods include hypersensitive reactions, nausea and other untoward side effects. Such side effects may result from application of strong concentrations of bleaching agent to the dental arches of a patient who is unaccustomed to teeth bleaching. To date, no dental agents have been derived to alleviate or attenuate such and other contraindications.

Nor have compositions been derived to generally improve the condition of the teeth and mouth, regardless of whether the dentition have been subject to whitening or other of any other dental procedure.

Thus, there exist many problems with devices for delivering home bleaching agents which are presently available. Conventional rigid or custom-fabricated dental appliances require time-consuming and expensive dentist office visits, dental laboratory tests and fitting of each patient's dentition. Furthermore, any changes in the surface of the patient's teeth, such as fillings, crowns, and other accidental or therapeutic alterations of the dentition, would affect the fit of the rigid custom dental appliance and warrant repeating the entire fabrication procedure. Refabrication of the splint may also be required in the event of subsequent rebleaching.

Still further drawbacks with systems utilizing known systems for treatment of dental arches result improper dispensation of agent into dental appliances, particularly when the agent is dispensed by patients who are typically inexperienced and unaware of the importance of precision and infection control when self-administering such agents. As a result of such improper dispensing techniques, bleaching or other dental agent is often overfilled, spilled or incorrectly measured. Lack of aseptic technique increases the risk of contaminating the bleaching or other dental agent into an appliance. Patients who are self administering bleaching or other dental agents often fail to provide the careful maintenance, cleaning, and storage which is necessary for a rigid custom dental appliance to perform adequately throughout its entire service life.

Yet further problems result from patients' frequent dispersion of excessive bleaching or other dental agent into the dental appliance which is subsequently displaced from the appliance into the oral cavity and spilled into the mouth, ingested and introduced into the digestive system. Ingestion of significant amounts of bleaching agent may cause the user great discomfort and hypersensitive reactions. The resulting application of excessive bleaching agent and leakage of bleaching agent from the dental carriers or retainers may also cause gingival irritation, burning, edema, nausea and other allergic reactions. A patient may be thus subjected to excessive quantities of bleaching agent, particularly after the multiple treatments typically required to attain acceptable clinical results.

The aforementioned problems are not exhaustive but are mere examples of difficulties encountered with present devices. Therefore, it is apparent that there is a need for substantial improvement in dental treatments involving application of bleach or other dental agents to a patient's dentition and periodontal tissue.

SUMMARY OF THE INVENTION

The present invention provides a dental device for the treatment of dental arches and periodontal tissue addressing the drawbacks of the prior art, comprising a prefabricated dental appliance composed of a non-porous polymeric material having a trough for immersing the teeth of the dental arch, the dental appliance being adaptable to fit a range of variously sized dental arches, and a premeasured amount of bleaching and/or other dental agent, which may be predispensed within the trough of the disposable dental appliance. The dental appliance of the present invention may be packaged to enclose individual or multiple units. The predispensed dental agent may be predispensed within the packaged appliances, or be sealed in the trough of the dental appliance.

Alternatively, the predetermined amount of dental agent may be packaged in a separate container located adjacent to the trough orifice so that the dental agent is capable of being directly expelled into the trough of dental appliance when the seal is opened. As further described below, the packaging may also contain multiple dental appliances with predispensed dental agent. The dental agent may be sealed in a separate dispenser, preferably a syringe, but may also comprise other types of vials or pumps.

An embodiment of present system for treatment of the dental arches and periodontal tissue thus provides for application of a dental agent in one simple step, after the appliance is removed from the package. The simple administration of bleaching agent according to the present invention both optimizes hygiene and minimizes the risk of untoward side effects, by preventing spillage and contamination of the agent. The utilization of premeasured and predispensed dental agent further provides a virtually foolproof method for accurate delivery advantages of bleaching or other agents to dentition and periodontal tissue.

This dental appliance is composed of a soft, flexible polymer material, such as biocompatible polyvinyl chloride, ethyl vinyl acetate, and urethanes that may be blended with rubber, or other similar biocompatible polymers, which adapts to the dental arches and surrounding gingival tissue and thereby avoids invasion or irritation. The composition and configuration of packaging for the dental appliance may vary. The packaging is preferably composed of a rigid material, such as polypropylene, polybutylene or similar material, which is molded into a cavity or cavities adapted to the dental appliance so as to maintain its intended configuration when being applied to a patient's dental arches.

As used herein, a prefabricated dental appliance is a dental appliance which is subject to mass production of a universal size or sizes adaptable to fit a range of variably sized dental arches, and is not custom fitted to individual dental arches.

As used herein, a dental agent is any composition containing a pharmaceutical, bleaching or lightening agent, a nutrition supplement, or other biocompatible compound capable of improving the condition of or minimizing untoward side effects of bleaching or other dental treatments. Such compounds may include, but are not limited to, dental bleaching agents, such as carbamide peroxide, antioxidants, such as vitamin E, healing agents such as aloe vera, surfactants for coating the surface of the teeth with a whitener, such as poloaxmer, anti-caries agents such as fluoride, or even dental scrubs which can be brushed to polish the teeth after the treatment of the present invention has been applied.

The present invention further provides a desiccant in or on the packaging to absorb moisture and to keep the dental agent anhydrous in composition. The desiccant is a hygroscopic substance, such as a calcium carbonate, calcium chloride, alumina, silica gel or granules, zinc chloride, or other drying substance. Such substances absorb water vapor from the surrounding atmosphere to maintain a dry, anhydrous condition. Inclusion of desiccant is particularly advantageous in maintaining the efficacy of carbamide peroxide. Water causes carbamide peroxide to break down into urea and hydrogen peroxide. Therefore, reduced water vapor affords a longer shelf life while maintaining higher concentrations of carbamide peroxide. The net result is a more efficacious whitening product secondary to improved shelf life and greater concentration of carbamide peroxide. In a preferred embodiment of the present invention, the desiccant is fixed or laminated to an inner surface of the packaging. The laminating mentioned is permeable to water vapor. Alternatively, the desiccant may be provided in a blister pack.

In one embodiment of this invention, the dental appliance is vacuum sealed within the packaging. Alternatively, an inert gas, including, for example, a noble gas such as helium, argon or neon, is injected within the packaging that encloses the dental appliance.

The present invention features a dental appliance wherein a first strip of open cell foam is affixed along the frontal inner wall of the dental appliance and a second strip of open cell foam is affixed along the rear inner wall of the dental appliance such that a reservoir cavity for containment of the dental agent is formed along the bottom of the trough of the dental appliance.

Alternatively, a strip of open cell foam may be affixed along the frontal inner wall of the trough of the dental appliance for contacting the anterior portion of the dental arch subject to treatment. Dental agent may be predispensed within the open cell foam affixed to the inner wall or walls of the dental appliance according to the present invention or be predispensed within a separate container which is located within or adjacent to the trough of the dental appliance.

In such and other embodiments of the present invention, the frontal inner wall surface of the trough can be recessed along substantially the entire frontal inner wall surface of the trough of the dental appliance so as to form a treatment chamber for contacting the anterior surface of the teeth subject to treatment.

A still further feature of the present invention includes a buffer region in the area around the periodontal tissue surrounding the teeth subject to treatment, the buffer region containing material to prevent the periodontal tissue from coming into contact with the active bleaching agent. The buffer region preferably contains a chemical compound capable of stabilizing or otherwise minimizing the potentially untoward side effects of the active bleaching agent. In another embodiment of the invention, the buffer region contains an adhesive, such as zinc oxide eugenol.

Yet another feature of the present invention includes application of other dental agents capable of imparting potential therapeutic effect or to minimize the risk of bleaching or other agents of having potentially untoward side effects upon the teeth and surrounding tissue. As previously defined, dental agents may include antioxidants such as vitamin E, surfactants for coating the surface of the teeth with a whitener such as poloaxmer, healing agents such as aloe vera, anti-caries agents such as fluoride, or even dental scrubs which can be brushed to polish the teeth after the treatment of the present invention has been applied.

An important advantage provided by the prefabricated dental appliance of the present invention includes elimination of the need for dental impressions and fabrication of a custom dental appliance, as it is designed to fit a range of variously sized dental arches. The appliance thus need not be prescription fitted or custom made, and thus may purchased over the counter. The capability for utilizing and maintaining sterile packaging and single use of the present invention may further minimize drawbacks attendant to bacterial contamination and cleaning.

The device and method of the present invention provides the further benefit of facilitating localized application of medicinal compounds, such as bleaching agents, which may be associated with untoward side effects, as discussed above. For instance, targeting the treatment surface on just the anterior surface of the teeth when applying bleaching procedures to the visible anterior surface of the teeth provides the advantage of requiring less bleaching agent and minimizing the risk of hypersensitive, or other untoward side effects.

A method of treatment according to this invention for treating dental arches and surrounding tissue according to the present invention includes the steps of selecting a prefabricated dental appliance composed of a non-porous polymeric material adaptable to fit a range of variously sized dental arches having a trough for immersing the teeth and periodontal tissue of the dental arch which contains a dental agent, and applying the dental appliance so as to immerse a user's dental arches in the dental agent.

The dental agent of the present invention may include an antioxidant, such as vitamin E. It may further include aloe vera. Such dental agents can be applied together with or separately from bleaching or other dental agents.

A further method of the present invention includes a lightening treatment regiment wherein progressively higher concentrations of bleaching agent are applied to the dental arches. The method of treatment may include administering:

(1) between 2 and 10 applications of bleaching agent comprised of between about 5% and about 15%, and preferably about 10%, carbamide peroxide or other bleaching agent; (2) between 2 and 10 applications of bleaching agent comprised of between about 8% and about 18%, and preferably about 12.5%, carbamide peroxide or other bleaching agent; and (3) between 2 and 10 applications of bleaching agent comprised of between about 10% and about 20%, and preferably about 15%, carbamide peroxide or other bleaching agent. A further feature of this embodiment of the method according to the present invention, as with other embodiments discussed above, includes application of other dental agents, as defmed above, with one or more bleaching application treatments.

BRIEF DESCRIPTION OT THE DRAWINGS

FIG. 1 depicts a perspective view of the dental appliance in accordance with the present invention;

FIG. 1A provides a cross-sectional view of the device of the present invention, taken along line 1—1 of FIG. 1 shown in relation to teeth positioned for immersion therein;

FIG. 2 provides a transverse cross-sectional view of the present invention as actually applied to teeth;

Figure 10:
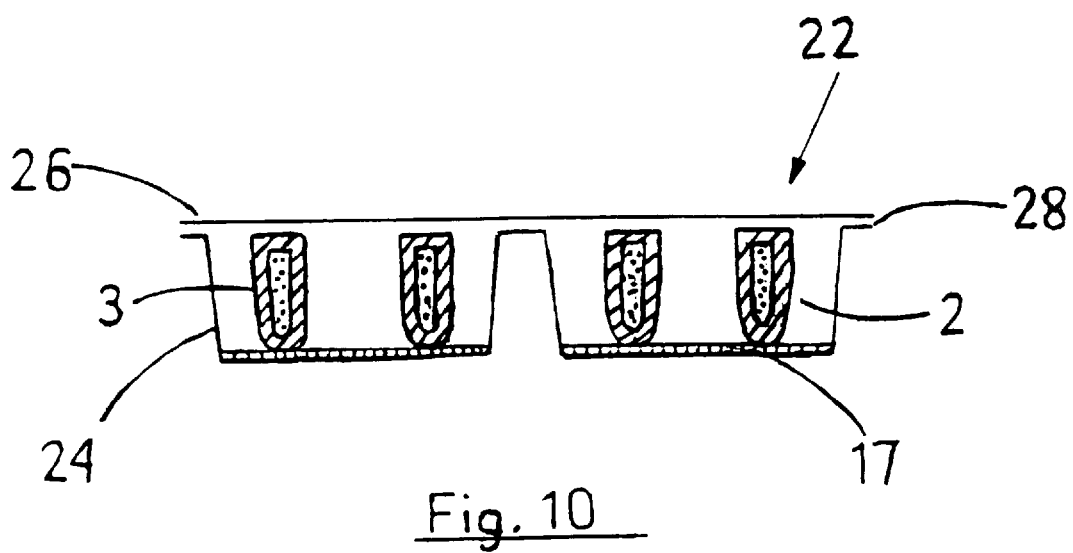

FIG. 10 provides a transverse cross-sectional view of the multiple unit package containing dental appliances having predispensed dental agent.

DETAILED DESCRIPTION OF THE PREFERRED EMBODIMENTS

Figure 1:
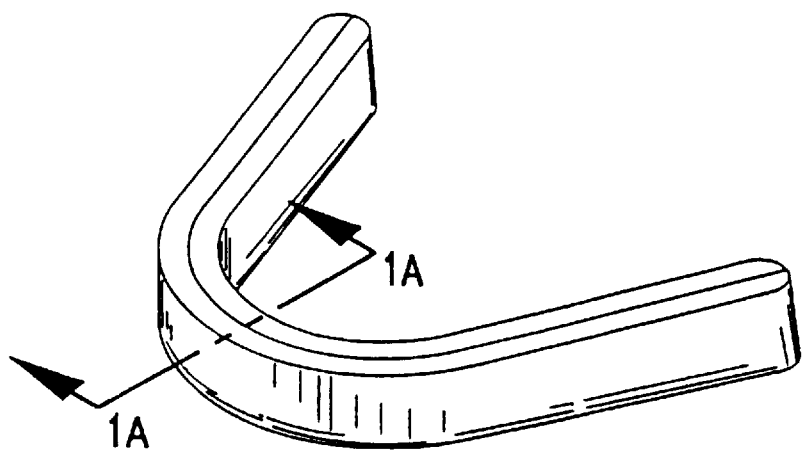
Figure 2:
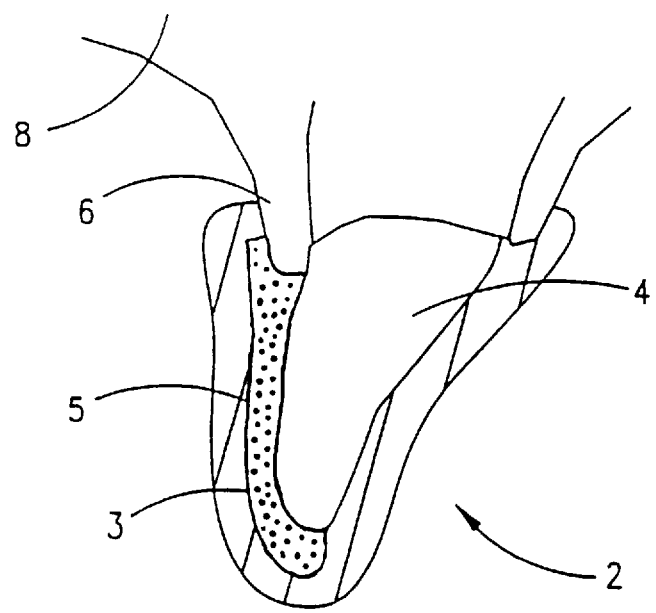

Referring to the drawings, the device shown in FIGS. 1–2 consists of a pre-fabricated U-shaped dental appliance 2 having a trough along the long, horizontal axis of the dental appliance 2 containing a premeasured quantity of dental agent 3 for immersing the teeth 4 which are subject to treatment. The dental appliance 2 is fabricated from a non-porous polymer.

Figure 3:
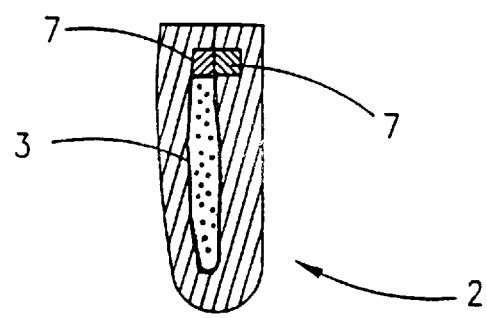
FIG. 3 depicts a transverse cross-sectional view of the dental appliance of the present invention which contains a buffer region.
Figure 4:
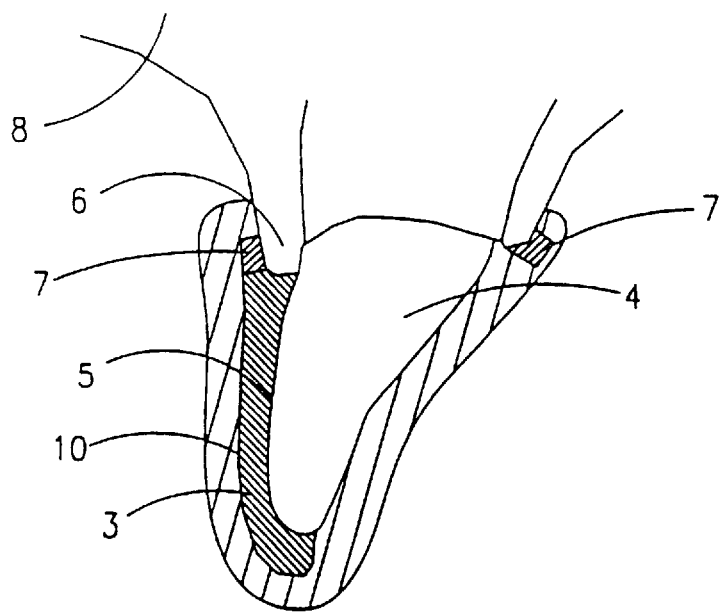
FIG. 4 depicts a transverse cross-sectional view of the dental appliance of the present invention having an open cell foam containing a bleaching agent affixed to a frontal inner wall of the trough.

FIGS. 3–4 depict dental appliance 2 as it appears in relation to the teeth 4 of the dental arch in actual practice. In the procedure utilized in practicing the present invention, first, an appropriate prefabricated, disposable dental appliance 2 which approximately fits around the relevant patient's dental arches is selected. Dental appliance 2 is composed of polyvinyl acetate, a flexible and soft material that does not invade or irritate the gingival tissue surrounding the dental arches. As shown, the dental appliance 2 may be packaged with a premeasured quantity of dental agent 3 predispensed in the trough. Dental agent 3 preferably includes a bleaching agent, such as 10% carbamide peroxide, and may alternatively include an antioxidant such as vitamin E, a whitening surfactant for coating the teeth such as poloaxmer, fluoride, aloe vera, a dental scrub, or any other agent for treatment of the teeth and/or the surrounding periodontal tissue.

Figure 1A:
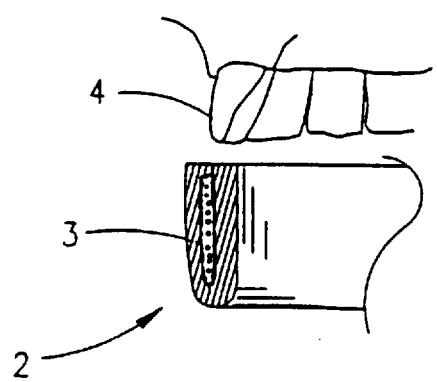

The dental appliance 2 is next removed from the packaging and delivered to the teeth 4. Delivery of the dental agent 3 is effected by positioning the dental appliance 2 intraorally with the trough aligned in a parallel fashion to the edges of the teeth 4 as shown in FIGS. 1A and 2. In order to correctly place the dental appliance 2 over the teeth 4, the trough is pushed in the direction of the gingiva 6 and soft tissue 8, also referred to herein as periodontal tissue, surrounding the dental arch toward and then around the edges of the teeth. Correctly placed, the dental appliance 2 covers the teeth 4 and gingiva 6 of the dental arch as illustrated in FIG. 3, and provides a system whereby the dental appliance 2 delivers a premeasured quantity of dental agent 3 to the teeth of the dental arch in a single, simple step, after being unpackaged.

Figure 5:
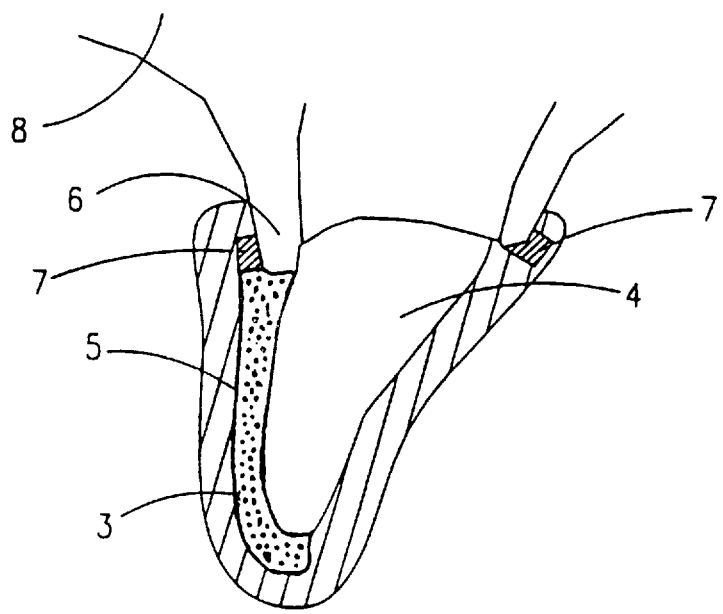
FIG. 5 illustrates a transverse cross-sectional view of the dental appliance of the present invention having a trough which is shaped such that bleaching agent is concentrated on the anterior of the teeth.

As shown in FIGS. 2, 4, and 5, teeth 4 and gingiva 6 are embedded and intimately interface with dental agent 3. Correct placement of dental appliance 2 results in a gingival interface formed about the orifice of the trough which facilitates localization of dental agent 3 within target area 5.

FIG. 3 depicts an embodiment of the present invention including buffer region 7 which protects against the potential untoward side effects of dental agent 3. Buffer region 7 may include any biocompatible agent capable of stabilizing dental bleaching or other dental agents such as carbamide peroxide and other peroxy compound, e.g., antioxidants such as vitamin E, and may also include zinc oxide eugenol. Buffer region 7 may further include any composition capable of minimizing potential untoward side effects of dental agent 3.

FIG. 4 illustrates one embodiment of the present invention wherein an open cell foam 10 is laminated or otherwise affixed to an inner wall of the dental appliance 2. The open cell foam 10 thus forms a matrix for application of the dental agent 3.

FIG. 5 depicts an embodiment of the present invention wherein the dental appliance 2 is formed so that the dental agent 3 is confined to the frontal inner wall of the dental appliance 2 adjacent to target area 5 of the anterior surface of the teeth 4, when properly used. A reaction vessel is thus formed localizing dental agent 3 to the anterior surfaces of the teeth 4.

Figure 6:
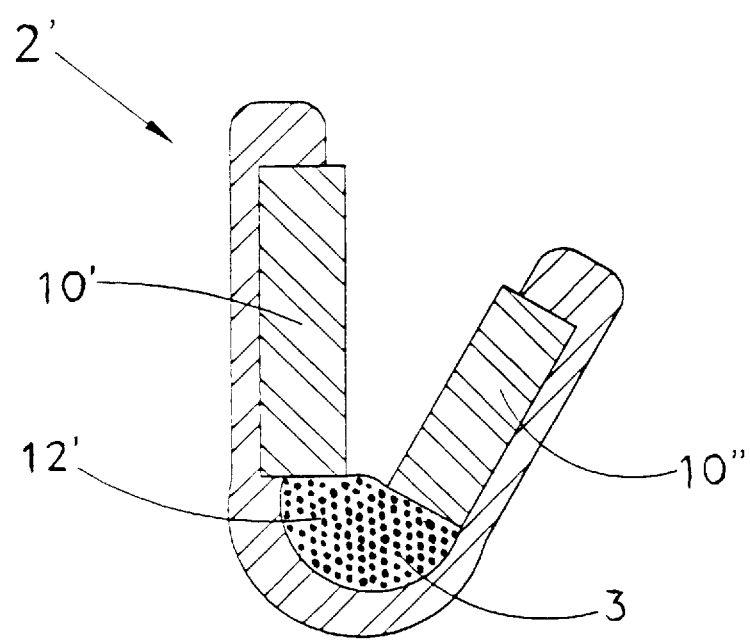
FIG. 6 illustrates a transverse cross-sectional view of the dental appliance of the present invention having a strip of open cell foam affixed along the inner front and rear walls of the dental appliance.

FIG. 6 illustrates another embodiment of the present invention wherein dental appliance 2 includes a first strip of open cell foam 10' that is attached along the frontal inner wall of the dental appliance and a second strip of open cell foam 10" that is attached along the rear inner wall of the dental appliance. Thus, a reservoir cavity 12 for containment of the dental agent is formed along the bottom of the trough of the dental appliance. In this embodiment, dental agent 3 is predispensed in reservoir cavity 12. When teeth 4 are placed in reservoir cavity 12, dental agent 3 is forced upward into open cell foam strips 10' and 10", and thus delivered to the treatment region targeted by the strips in a contained and efficient manner.

Figure 7:
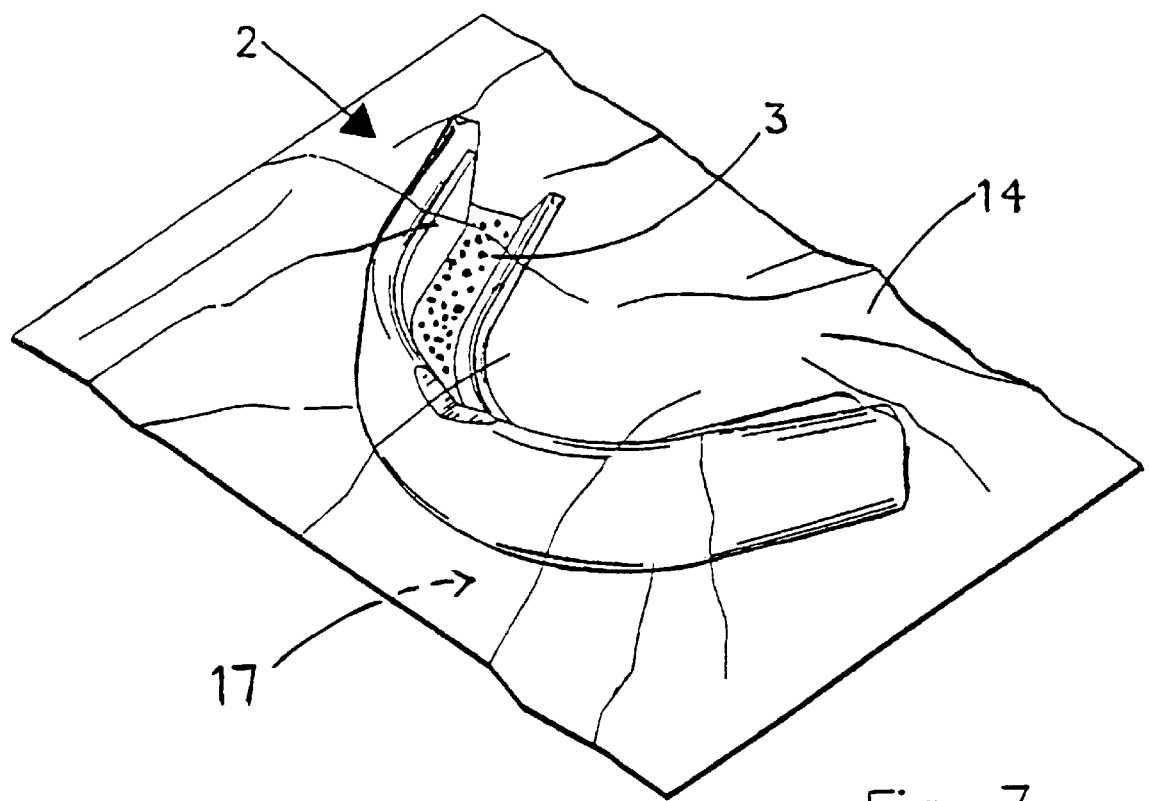
FIG. 7 depicts a top perspective view of the device of the present invention packaged so as to seal the bleaching agent in the dental appliance.
Figure 7A:
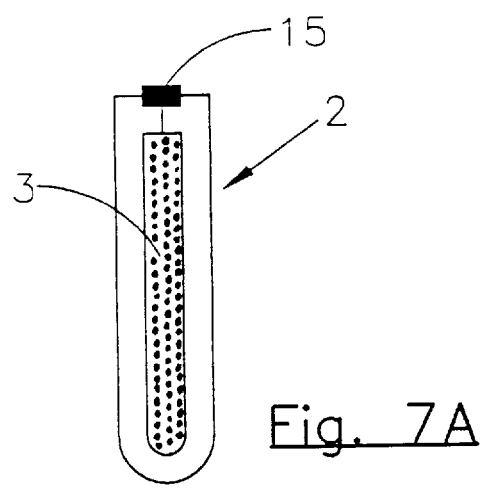
FIG. 7A depicts a transverse cross-sectional view of the device of the present invention wherein the packaging includes sealing the rim of the trough orifice.

FIG. 7 depicts an embodiment of the present invention wherein packaging 14 envelopes the entire dental appliance 2 which contains dental agent 3. Alternatively, is as shown in FIG. 7A, dental appliance 2 can include seal 15 of the rim of the trough of dental appliance 2 which effectuates containment of dental agent 3 therein. Laminated on inner surface of packaging 14 is a desiccant 17 to absorb any moisture that might condense within the systems and thereby keep the dental agent anhydrous.

Figure 8:
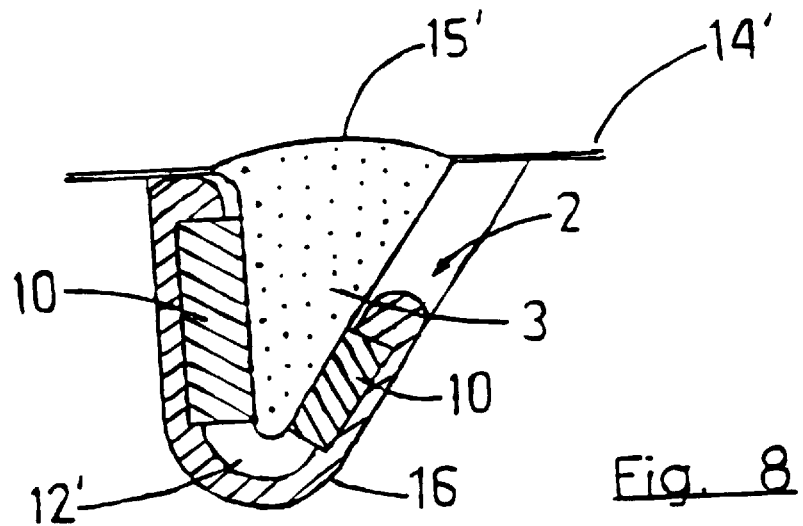
FIG. 8 depicts a transverse cross-sectional view of the device of the present invention wherein premeasured bleaching agent is sealed in a container adjacent to the trough for dispensation into the dental appliance.
Figure 8A:
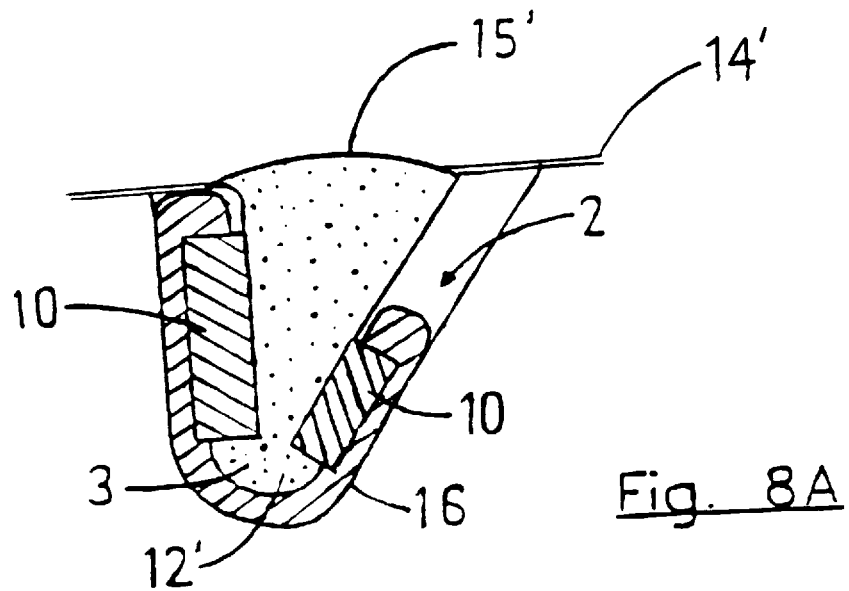
FIG. 8A depicts a transverse cross-sectional view of the device of the present invention wherein the premeasured bleaching agent compartment is unsealed and delivered in the reservoir cavity of the dental appliance.

FIG. 8 depicts another embodiment of the present invention wherein dental appliance 2 is encased in packaging 14'. In this embodiment, dental agent 3 may be contained in a compartment walled off by packaging 14' located adjacent to the trough of dental appliance 2. Dental agent 3 is sealed within the compartment by seal 15' adjoined to packaging 14' on either side of the upper surface of dental appliance 2 and by aperture seal 16, which is composed of a substantially thinner and more easily ruptured polymer substance than seal 15'. Preferably, aperture seal 16 and seal 15' are composed of polyvinyl chloride having lesser and greater densities, respectively. Application of pressure on seal 15' at the rim of the orifice of the trough of dental appliance 2 or squeezing together the frontal and rear walls of dental appliance 2 triggers rupture of the easily ruptured aperture seal 16, and thereby causes expulsion of the premeasured amount of dental agent 3 directly into reservoir cavity 12', as illustrated in FIG. 8A.

Figure 9:
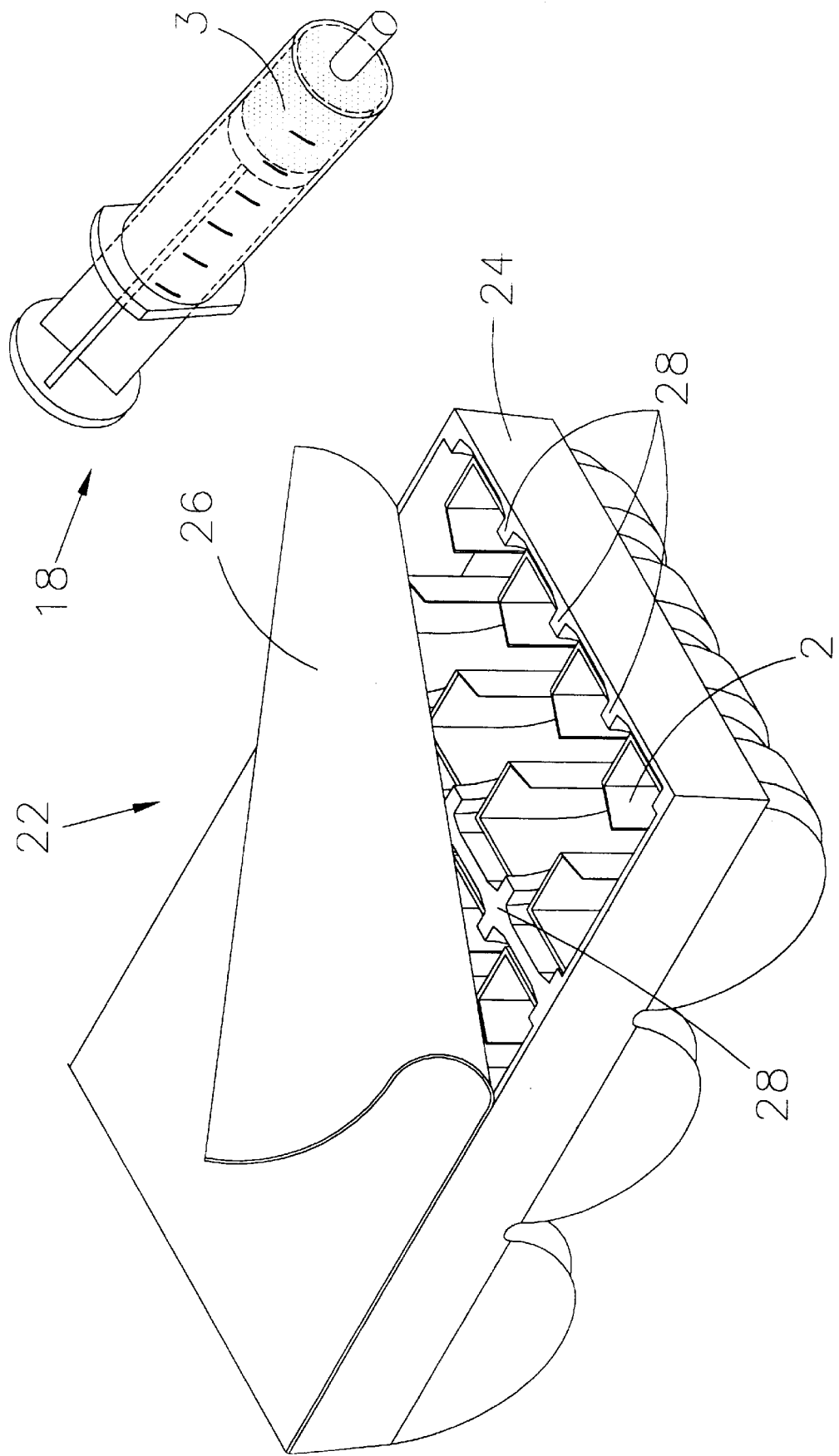
FIG. 9 depicts a perspective view of the multiple unit package of the present invention, wherein the dental agent is contained in a syringe.

In another embodiment of the present invention that is depicted in FIG. 9, the premeasured amount of dental agent 3 is contained in a separate syringe 18. The container may alternatively be a pump or other similar calibrated dispenser. In an alternative embodiment of this invention, syringe 18 may be calibrated to deliver multiple aliquots of dental agent 3.

This embodiment of the "kit" further includes packaging 22 enclosing multiple dental appliances 2 with predispensed dental agent 3. Packaging 22 is composed of a lower rigid receptacle 24 and an upper flexible sheet 26. As shown, receptacle 24 is composed of polypropylene, that is vacuum molded to form multiple cavities, or cells, having two elongated parallel U-shaped walls adjoined in a rounded, or U-shaped, bottom surface configured to form a support dental appliance 2, without predispensed dental agent 3. Protruding from the top of the walls surrounding each of the cavities are ledges 28. Sheet 26 is heat sealed so that surfaces contacting ledges 28 are detachably adhered, thereby keeping dental appliance 2 within the cells of receptacle 24. Sheet 26 is easily detached by manually pulling it off ledges 28 of receptacle 24.

FIG. 10 is a transverse cross-sectional view of packaging 22, wherein individual dental appliances 2 have predispensed dental agent 3, and desiccant 17 is placed at the bottom surface of each cell thereof. Disposal predispensed dental appliances 2 are placed on top of the desiccant 17, which thereby creates a water gradient from the contents within the each packaging cell to desiccant 17. Thus placing desiccant 17 within each packaging cell minimizes the amount of water vapor in each cell, thereby reducing the available water for penetration into and possibly destabilizing dental agent 3. Alternatively, desiccant may be affixed or laminated to the surface of sheet 26 facing dental appliance 2.

It is to be understood that the present invention is not intended to be limited to the exact details of construction, operation, materials or embodiments shown and described herein, as obvious modifications and equivalents will be apparent to one skilled in the art. For example, the dental appliance of the present invention could be applied to facilitate the delivery to the teeth of other therapeutic agents. This disclosure is intended to cover all alternatives, modifications, and equivalents as may be included within the spirit and scope of the invention as defined by the appended claims.

The following claims represent the scope of this invention to the extent that it is subject to such delimitations. It will be appreciated by those skilled in the art that the anticipated uses and embodiments of the present invention are not amenable to precise delineation, but may vary from the exact language of the claims. Thus, the following claims are drawn not only to the explicit limitations, but also to the implicit embodiments embraced by the spirit of the claims.

We claim:

1. A device for treatment of dental arches and periodontal tissue, comprising:
   (a) a dental appliance composed of a non-porous flexible polymer that minimizes irritation of periodontal tissue surrounding the dental arches, the dental appliance having a trough for immersing the teeth of the dental arches in a premeasured aliquot of a dental a gent, the dental appliance being adaptable to fit a range of variously sized dental arches; and
   (b) packaging means for sealing the dental appliance, whereby the dental appliance is heat sealed so as to provide a closed, single-use system for application of the dental agent, wherein the packaging means encloses a vacuum.

2. A device for treatment of dental arches and periodontal tissue, comprising:
   (a) a dental appliance composed of a non-porous flexible polymer that minimizes irritation of periodontal tissue surrounding the dental arches, the dental appliance having a trough for immersing the teeth of the dental arches in a premeasured aliquot of a dental agent, the dental appliance being adaptable to fit a range of variously sized dental arches; and
   (b) packaging means for sealing the dental appliance, wherein the dental appliance is heat sealed so as to provide a closed, single-use system for application of the dental agent; and
   (c) an inert gas enclosed within the packaging means, wherein the inert gas is selected from the group consisting essentially of helium, argon, and neon.

3. A device for treatment of dental arches and periodontal tissue, comprising:
   (a) a dental appliance composed of a non-porous flexible polymer that minimizes irritation of periodontal tissue surrounding the dental arches, the dental appliance having a trough for immersing the teeth of the dental arches in a premeasured aliquot of a dental agent, the dental appliance being adaptable to fit a range of variously sized dental arches; and
   (b) packaging means enclosing the dental appliance, wherein the packaging means comprises a lower rigid receptacle comprised of one or more U-shaped cavities, each U-shaped cavity having a first and a second wall integrally adjoined to a bottom surface configured to support a dental appliance, the first and second walls further having ledges protruding outwardly therefrom; and (c) a flat sheet having an upper surface and a lower surface, the sheet being heat sealed so the lower surface is detachably affixed to the ledges of the receptacle, thereby enclosing the dental appliance within the U-shaped cavity of the receptacle.

4. The device of claim 3, wherein the receptacle comprises polypropylene.

5. The device of claim 3, wherein the receptacle comprises polybutylene.

6. The device of claim 3, wherein the dental agent is predispensed in a sealed container placed within the trough of the dental appliance in a manner whereby the dental agent is capable of being directly expelled into the trough of the dental appliance when the seal is opened.

7. The device of claim 3, wherein an open call foam containing the dental agent is affixed along an anterior portion and not a posterior portion of an inner wall of the dental appliance so as to concentrate the contact area in the anterior portion of the dental arch subject to treatment.

8. The device of claim 3, further comprising a desiccant laminated on the packaging.

9. The device of claim 3, further comprising a desiccant enclosed within the packaging, wherein the desiccant is a hygroscopic substance selected from the group consisting essentially of calcium carbonate or silica.

10. The device of claim 3, further comprising a vial containing a premeasured amount of dental agent composed partially from a member selected from the group consisting essentially of carbamide peroxide, vitamin E, aloe vera, fluoride, or poloaxmer.

11. A package for a dental appliance that is adaptable to fit a range of variously sized dental arches, comprising:

(a) a lower rigid receptacle comprised of one or more U-shaped cavities, each U-shaped cavity having a first and a second wall integrally adjoined to a bottom surface configured to support a dental appliance, the first and second walls further having ledges protruding outwardly therefrom; and (b) a flat sheet having an upper surface and a lower surface, the sheet being heat sealed so the lower surface is detachably affixed to the ledges of the receptacle, thereby enclosing the dental appliance within the U-shaped cavity of the receptacle.

12. The package of claim 11 wherein the receptacle comprises polypropylene.

13. The package of claim 11, further comprising a dispenser containing a predetermined amount of a dental agent, and wherein the receptacle is further molded to form a container for a dispenser.

14. The package of claim 11, further comprising a syringe containing a predetermined amount of a dental agent.

15. The package of claim 11, further comprising a syringe which is calibrated to dispense successive predetermined aliquots of a dental agent.

* * * * *